US00PP19934P2

(12) United States Plant Patent
Davis

(10) Patent No.: US PP19,934 P2
(45) Date of Patent: Apr. 21, 2009

(54) ***BUDDLEIA* PLANT NAMED 'STELLAR PINK'**

(50) Latin Name: *Buddleia davidii*
Varietal Denomination: Stellar Pink

(75) Inventor: Richard Eaton Davis, Locustville, VA (US)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 12/151,754

(22) Filed: May 8, 2008

(51) Int. Cl.
*A01H 5/00* (2006.01)

(52) U.S. Cl. ..... Plt./242
(58) Field of Classification Search ..... Plt./242
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Buddleia* plant named 'Stellar Pink', characterized by its upright and relatively compact plant habit; freely flowering habit; intense dark pink-colored flowers; and good garden performance.

2 Drawing Sheets

Botanical designation: *Buddleia davidii.*
Cultivar denomination: 'Stellar Pink'.

BACKGROUND OF THE INVENTION

The present invention relates to a new and distinct cultivar of *Buddleia,* botanically known as *Buddleia davidii* and hereinafter referred to by the name 'Stellar Pink'.

The new *Buddleia* is a product of a planned breeding program conducted by the Inventor in Locustville, Va. The objective of the breeding program was to create new compact *Buddleias* with attractive flower coloration.

The new *Buddleia* originated from a cross-pollination made by the Inventor in July, 2003 in Locustville, Va., of *Buddleia davidii* 'Pink Delight', not patented, as the female, or seed, parent with *Buddleia davidii* 'Royal Red', not patented, as the male, or pollen, parent. The new *Buddleia* was discovered and selected by the Inventor as a single flowering plant within the progeny of the stated cross-pollination in a controlled greenhouse environment in Locustville, Va. in August, 2004.

Asexual reproduction of the new *Buddleia* by cuttings in a controlled greenhouse environment in Locustville, Va. since August, 2005, has shown that the unique features of this new *Buddleia* are stable and reproduced true to type in successive generations.

SUMMARY OF THE INVENTION

The new *Buddleia* has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Stellar Pink'. These characteristics in combination distinguish 'Stellar Pink' as a new and distinct cultivar of *Buddleia:*

1. Upright and relatively compact plant habit.
2. Freely flowering habit.
3. Intense dark pink-colored flowers.
4. Good garden performance.

Plants of the new *Buddleia* differ from plants of the female parent in the following characteristics:

1. Plants of the new *Buddleia* are more compact than plants of 'Pink Delight'.
2. Plants of the new *Buddleia* have darker pink-colored flowers than 'Pink Delight'.

Plants of the new *Buddleia* differ from plants of the male parent in the following characteristics:

1. Plants of the new *Buddleia* and 'Royal Red' differ in leaf color as plants of 'Royal Red' have darker green-colored leaves.
2. Plants of the new *Buddleia* have lighter-colored flowers than 'Royal Red'.

Plants of the new *Buddleia* can be compared to plants of *Buddleia davidii* 'Peacock', not patented. In side-by-side comparisons conducted in Locustville, Va., plants of the new *Buddleia* and 'Peacock' differed in the following characteristics:

1. Plants of the new *Buddleia* were more compact than plants of 'Peacock'.
2. Plants of the new *Buddleia* had more intense pink-colored flowers than plants of 'Peacock'.

BRIEF DESCRIPTION OF THE PHOTOGRAPHS

The accompanying colored photographs illustrate the overall appearance of the new *Buddleia,* showing the colors as true as it is reasonably possible to obtain in colored reproductions of this type. Colors in the photographs may differ slightly from the color values cited in the detailed botanical description which accurately describe the colors of the new *Buddleia.*

The photograph on the first sheet comprises a side perspective view of a typical flowering plant of 'Stellar Pink' grown in an outdoor nursery.

The photograph on the second sheet is a close-up view of typical inflorescences of 'Stellar Pink'.

DETAILED BOTANICAL DESCRIPTION

The aforementioned photographs and following observations, measurements and values describe plants grown in Locustville, Va., under commercial practice during the summer and early autumn in an outdoor nursery with day temperatures ranging from 14° C. to 30° C. and night temperatures ranging from 5° C. to 16° C. Plants were about four years old when the photographs and description were taken. In the following description, color references are made to The Royal Horticultural Society Colour Chart, 2001 Edition, except where general terms of ordinary dictionary significance are used.

Botanical classification: *Buddleia davidii* 'Stellar Pink'.

Parentage:

*Female, or seed, parent.*—*Buddleia davidii* 'Pink Delight', not patented.

*Male, or pollen, parent.*—*Buddleia davidii* 'Royal Red', not patented.

Propagation:

*Type.*—By cuttings.

*Time to initiate roots plant, summer.*—About 10 to 14 days at 21° C. to 24° C.

*Time to initiate roots plant, winter.*—About two to three weeks at 16° C. to 18° C.

*Time to produce a rooted plant, summer.*—About 30 days at 21° C. to 24° C.

*Time to produce a rooted plant, winter.*—About 45 days at 16° C. to 18° C.

*Root description.*—Fibrous; white in color.

*Rooting habit.*—Freely branching, dense.

Plant description:

*Plant form/habit.*—Deciduous perennial shrub. Upright and relatively compact plant habit; outwardly spreading habit; broad inverted triangle; moderately vigorous growth habit.

*Plant height.*—About 59 cm.

*Plant width (spread).*—About 62.8 cm.

*Lateral branches.*—Quantity: About five main branches each with about six lateral branches per plant. Length: About 14 cm. Diameter: About 2.5 mm. Internode length: About 3.3 cm. Strength: Strong. Texture: Densely pubescent. Color, developing: Close to 143A to 143B; pubescence, close to 191A to 191B. Color, mature: Close to 199D.

Foliage description:

*Arrangement.*—Opposite, simple.

*Length.*—About 9.6 cm.

*Width.*—About 2.9 cm.

*Shape.*—Lanceolate.

*Apex.*—Acute.

*Base.*—Attenuate.

*Margin.*—Finely serrate.

*Texture, upper surface.*—Smooth, glabrous.

*Texture, lower surface.*—Densely pubescent.

*Venation pattern.*—Pinnate.

*Color.*—Developing leaves, upper surface: Close to 189A; towards the apex, close to 137A. Developing leaves, lower surface: Close to 192C. Fully expanded leaves, upper surface: Close to 137A; main veins, close to 144A to 144B; secondary veins, close to 139A. Fully expanded leaves, lower surface: Close to 194A; venation, close to 194B to 194C.

*Petiole.*—Length: About 4 mm. Diameter: About 1.5 mm. Texture, upper and lower surfaces: Smooth, glabrous. Color, upper and lower surfaces: Close to 194C.

Flower description:

*Flower type/habit.*—Single rotate and salverform flowers arranged in compound terminal panicles; flowers face upright and outward. Panicles roughly conical in shape. Freely flowering habit with about 350 flower buds and flowers developing per inflorescence.

*Fragrance.*—Moderately fragrant, sweet.

*Natural flowering season.*—Continuously flowering from July until September in Locustville, Va. Flowers not persistent.

*Postproduction longevity.*—Flowers last about ten days on the plant.

*Flower buds.*—Height: About 9 mm. Diameter: About 2 mm. Shape: Narrowly spatulate. Color: Close to 71B; towards the base, close to N77B.

*Inflorescence height.*—About 13.5 cm.

*Inflorescence diameter.*—About 3.5 cm.

*Flower diameter.*—About 6 mm.

*Flower depth.*—About 1.1 cm.

*Petals.*—Quantity per flower: Typically four in a single whorl; petals fused into a narrow tube. Length: About 1.1 cm. Lobe width: About 2 mm. Shape: Narrowly spatulate. Apex: Obtuse, irregular. Margin: Entire. Texture, upper and lower surfaces: Smooth, glabrous. Color: Developing petals, upper surface: Between 71C and 72B; tube, close to 176C to 176D. Developing petals, lower surface: Between 71C and 72B; tube, close to 58A. Fully expanded petals, upper surface: Close to N82A; tube, close to 24A. Fully expanded petals, lower surface: Close to 83D; tube, between 71C and 72B.

*Sepals.*—Quantity per flower: Typically four in a single whorl, fused towards the base; campanulate calyx. Length: About 3 mm. Width: About 0.5 mm. Shape: Ovate. Apex: Acute. Margin: Entire. Texture, upper and lower surfaces: Moderately pubescent. Color, developing sepals, upper and lower surfaces: Close to 146D. Color, fully expanded sepals, upper and lower surfaces: Close to 145A.

*Peduncles.*—Length: About 12.9 cm. Diameter: About 2 mm. Angle: Mostly erect. Strength: Moderately strong. Texture: Pubescent. Color: Close to 194B to 194C.

*Pedicels.*—Length: About 2 mm. Diameter: About 0.5 mm. Angle: About 50° to 80° from vertical. Strength: Moderately strong. Texture: Pubescent. Color: Close to 194B to 194C.

*Reproductive organs.*—Stamens: Quantity per flower: Typically four; filaments adnate to the corolla tube. Anther shape: Oblong. Anther length: About 0.75 mm. Anther color: Close to 4D. Pollen amount: Moderate. Pollen color: Close to 4C to 4D. Pistils: Quantity per flower: One. Pistil length: About 1.5 mm. Stigma shape: Club-shaped. Stigma color: Close to 150B. Style length: About 0.5 cm. Style color: Close to 187D. Ovary color: Close to 147D.

*Seed/fruit.*—Seed and fruit development have not been observed.

Disease/pest resistance: Plants of the new *Buddleia* have been not been observed to be resistant to pathogens and pests common to *Buddleia*.

Garden performance: Plants of the new *Buddleia* have been observed to have good garden performance and tolerate rain, wind and temperatures ranging from about −23° C. to about 40° C.

It is claimed:

1. A new and distinct *Buddleia* plant named 'Stellar Pink' as illustrated and described.

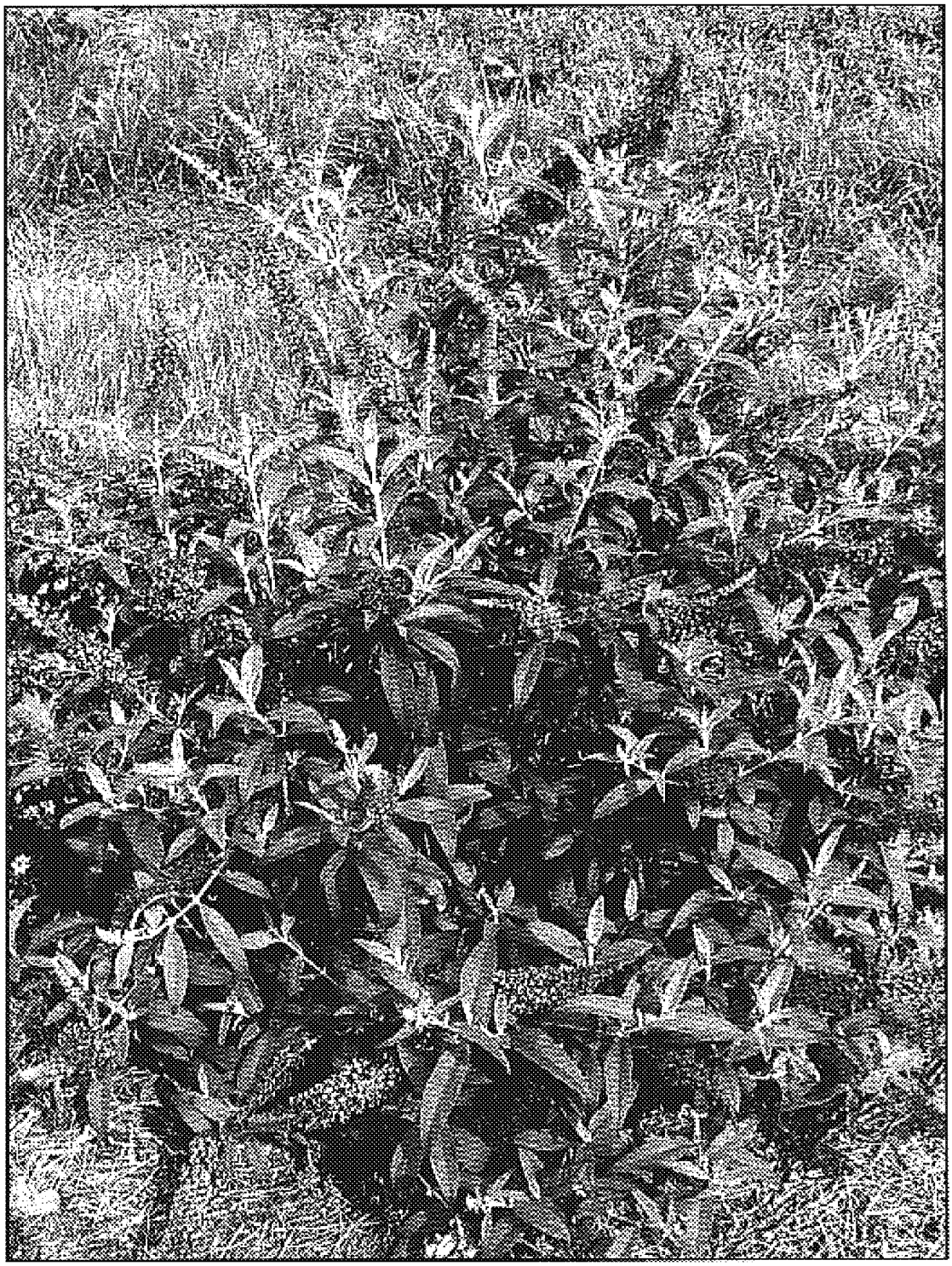

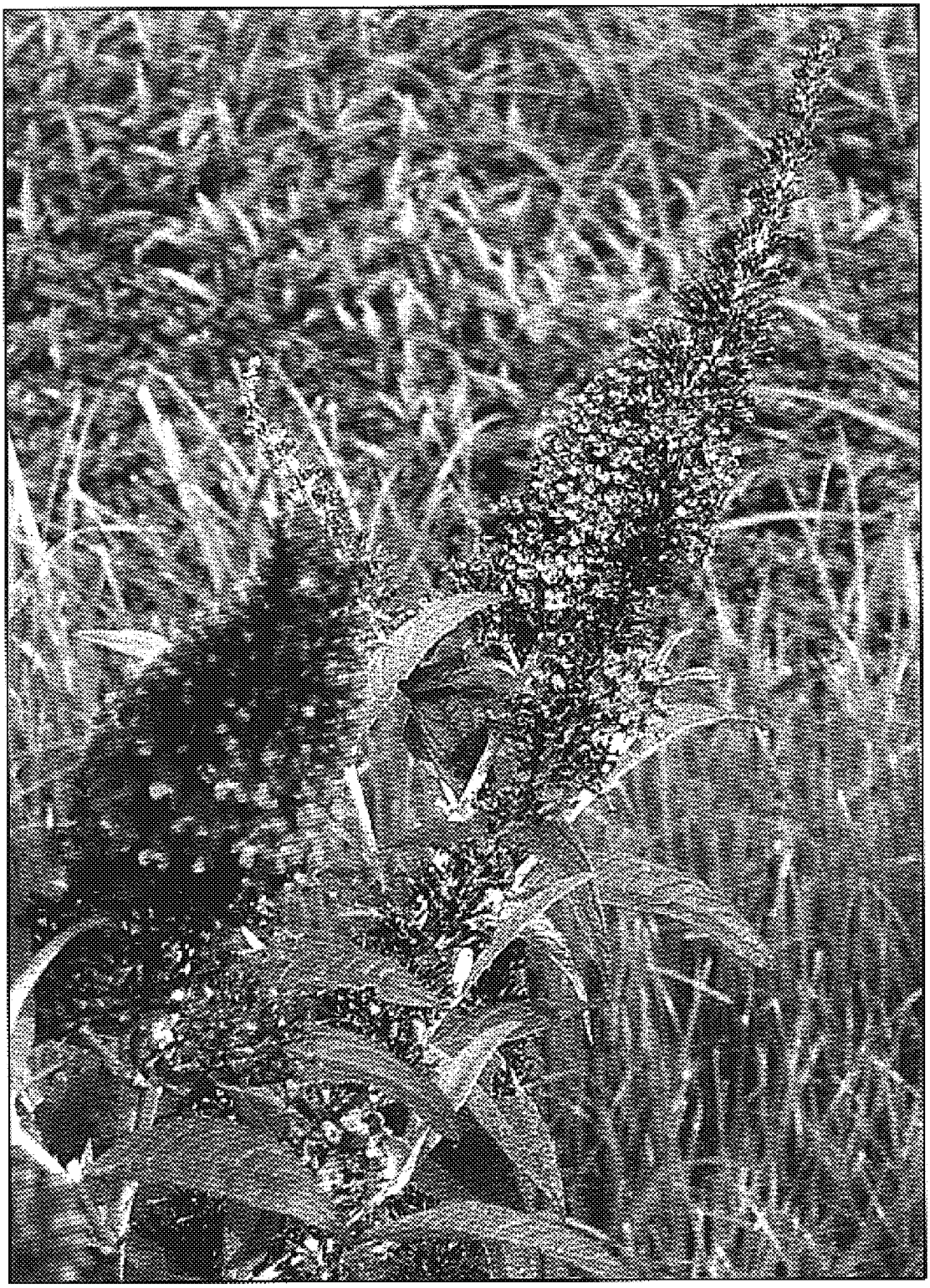

* * * * *